United States Patent [19]

Daoud

[11] Patent Number: 5,423,346
[45] Date of Patent: Jun. 13, 1995

[54] FLUID CONTAINER SHUT OFF VALVE

[75] Inventor: Adib G. Daoud, San Diego, Calif.

[73] Assignee: IVAC Corporation, San Diego, Calif.

[21] Appl. No.: 205,189

[22] Filed: Mar. 3, 1994

[51] Int. Cl.⁶ .................. F16K 31/22; F16K 33/00; A61M 5/168
[52] U.S. Cl. .................. 137/399; 137/433; 604/249; 604/254
[58] Field of Search .............. 137/397, 398, 399, 430, 137/433, 428; 604/251, 252, 253, 254, 249, 256

[56] References Cited

U.S. PATENT DOCUMENTS

| Re. 26,124 | 12/1966 | Koehn | 604/254 |
|---|---|---|---|
| 2,672,051 | 3/1954 | Butler | 73/861.55 |
| 2,693,801 | 11/1954 | Foreman | 137/433 |
| 2,729,212 | 1/1956 | Butler | 604/251 |
| 2,784,733 | 3/1957 | Martinez | 137/399 |
| 2,844,147 | 7/1958 | Beacham | 137/433 |
| 2,850,211 | 9/1958 | Fernandez | 604/254 |
| 2,879,784 | 3/1959 | Cutter | 137/192 |
| 2,907,325 | 10/1959 | Burke | 604/185 |
| 2,989,052 | 6/1961 | Broman | 604/124 |
| 3,035,575 | 5/1962 | Broman | 604/185 |
| 3,101,710 | 8/1963 | Koehn | 604/254 |
| 3,191,608 | 6/1965 | Licata | 137/433 |
| 3,207,372 | 9/1965 | Evans | 604/127 |
| 3,216,419 | 11/1965 | Scislowicz | 604/254 |
| 3,227,173 | 1/1966 | Bernstein | 137/451 |
| 3,454,036 | 7/1969 | Thompson | 137/444 |
| 3,625,211 | 12/1971 | Butler | 222/67 |
| 3,656,505 | 4/1972 | O'Brian | 604/254 |
| 3,756,233 | 9/1973 | Goldowsky | 604/254 |
| 3,896,733 | 7/1975 | Rosenberg | 604/4 |
| 3,949,745 | 4/1976 | Howell | 137/135 |
| 3,993,062 | 11/1976 | Jess | 137/183 |
| 4,000,738 | 1/1977 | Howell | 137/135 |
| 4,010,750 | 3/1977 | Howell | 137/135 |
| 4,037,596 | 7/1977 | LeFevre et al. | 138/44 |
| 4,055,176 | 10/1977 | Lundquist | 137/399 |
| 4,078,563 | 3/1978 | Tuseth | 137/433 |
| 4,079,736 | 3/1978 | Lundquist | 137/556 |
| 4,099,527 | 7/1978 | Howell | 137/135 |
| 4,103,686 | 8/1978 | LeFevre | 137/211 |
| 4,143,659 | 3/1979 | Biedermann | 141/113 |
| 4,175,558 | 11/1979 | Hess, III et al. | 604/127 |
| 4,178,927 | 12/1979 | Lundquist | 604/152 |
| 4,203,463 | 5/1980 | Ponlot et al. | 137/433 |
| 4,227,525 | 10/1980 | Lundquist | 604/126 |
| 4,640,306 | 2/1987 | Fan | 137/433 |
| 4,731,060 | 3/1988 | Catalano | 604/254 |
| 4,870,987 | 10/1989 | Cheng | 137/192 |
| 4,959,053 | 9/1990 | Jang | 604/254 |
| 5,031,654 | 7/1991 | Kobayashi | 137/192 |

FOREIGN PATENT DOCUMENTS

2161828 6/1972 Germany.

*Primary Examiner*—George L. Walton
*Attorney, Agent, or Firm*—Fulwider, Patton, Lee & Utecht

[57] ABSTRACT

A fluid shut off valve for use in a parenteral fluid administration set includes a disk floating in a fluid chamber that shuts off fluid flow when the fluid in the chamber decreases below a certain level. The chamber includes a valve stem at its lower end that has both a valve seat and an alignment member with an alignment surface on the top end thereof for guiding the disk into proper seating on the valve seat. The valve seat and floating disk have complementary engagement surfaces for also guiding the disk into proper seating on the valve seat. In one embodiment, the alignment member includes fins located both on the valve stem and on the inside wall of the chamber. Because of the configuration of the alignment member, dislodgement of the disk from the valve seat is made easier.

20 Claims, 7 Drawing Sheets

FIG. 10

FLUID CONTAINER SHUT OFF VALVE

BACKGROUND

The invention is generally related to devices to shut off the flow of fluids through a fluid conduit, and more particularly to a device that floats in a fluid contained in a reservoir, and when the fluid therein reaches a certain level, the device automatically closes an orifice in such reservoir to prevent further fluid flow, while in particular preventing passage of air therethrough.

In patient care facilities, infusion of a parenteral solution into a patient may be achieved by suspending an inverted bottle or fluid reservoir above the patient and interconnecting a fluid administration set between the reservoir and the patient. The administration set may include a vented penetrant to pierce the stopper of the reservoir and a transparent drip chamber connected in series with the administration set tubing, through which the rate of parenteral solution flow can be monitored. The distal end of the tubing is connected to a cannula that is inserted into a blood vessel of the patient. A pinch valve and/or pumping mechanism engaged with the tubing may be actuated to compress the walls of the tubing, thereby restricting fluid flow therethrough to regulate the flow to a selected rate.

In therapeutic fluid administration systems, it is important that introduction of air into a patient's blood vessel be limited. Should air be introduced into a blood vessel, a condition known as air embolism may result whereby an air bubble may form in such blood vessel causing a blood flow obstruction therein. Air embolism has proven fatal in some instances. Consequently, it is desirable to include an automatic shut off device within a fluid administration set that prevents air from being introduced into tubing leading to a patient's blood vessel; the shut off device being operative once the parenteral fluid contained in the fluid container of the administration set has been exhausted.

It is well known that therapeutic fluid administration sets including drip chambers are subject to being tilted to one side as fluid administration is being conducted. This may occur, for instance, when a patient is being transported to or from a patient care facility or when the patient is being moved to different locations within the facility. In addition, attendants may inadvertently set up the administration set in a tilted position. Therefore in order to be effective, a fluid shut off device must be capable of providing a reliable air tight seal even if the fluid administration set is tilted.

Other fluid shut off devices have been provided that include floating valve members such as balls or disks that seat on an outlet port to prevent the passage of air therethrough. It has been noted in some fluid shut off devices that include a floating ball that the ball may begin spinning and/or bobbing in the fluid at high fluid flow rates. The spinning of the ball caused by high flow rates appears to result in the ball bobbing in the fluid. Should the bobbing ball approach the valve seat too closely, it may actually seat prematurely and stop flow before emptying the fluid reservoir. An attendant would then need to dislodge the ball to resume flow. This may result in lost time that the patient could have received the medication from the reservoir.

A consideration pertinent to floating flow stop devices is that they must reliably shut off flow. The floating member must not be subject to binding or sticking in an open position and must be guided to properly engage the valve seat. Some manufacturers have taken the approach of providing a cage-like component that confines a floating disk to a limited range of movement over the outlet port to avoid sticking and improper seating. However, the inclusion of such a confinement cage increases the costs of manufacture of such a shut off valve making it less desirable.

A further consideration in the design of floating shut off valves is the ability to dislodge the seated floating member from the valve seat when needed to resume infusion. Ease of dislodging is desirable so that time is not wasted in attempting to pry the floating member off the seat. Preferably, the floating member should be dislodgable by a simple action of the attendant.

Another flow shut off device includes a floating disk disposed in a fluid chamber where the chamber has outer side walls shaped to provide alignment surfaces to the disk to properly align the disk into sealing contact with a valve seat. This approach requires a specially formed outer wall for the chamber making the retrofit or adaptation of existing straight walled chambers difficult. Additionally, shaped outer walls many times have the effect of strengthening the wall thereby making it more difficult to dislodge the sealing device from the valve seat by squeezing the walls together. Shut off devices having float containment cages may also interfere with the operator's attempts to dislodge the float member.

It is also desirable that the administration set including the fluid shut off device be made available as inexpensively as possible because such fluid administration sets are discarded after use.

Hence, those skilled in the art have recognized the need for a disposable administration set including a reliable fluid flow shut off device that provides an effective seal to prevent the passage of air. The shut off device should also be easily releasable when it is desired to resume flow. In addition, a device of this nature should be cost effective and easy to manufacture. The present invention meets these needs and others.

SUMMARY OF THE INVENTION

Briefly and in general terms, the present invention is directed to a fluid shut off valve that stops the passage of fluid through an outlet port of a fluid chamber when the fluid contained therein has been depleted to a certain level. In particular, the fluid shut off valve includes a valve seat formed on an outlet port and a floating disk member that engages the valve seat to prevent passage of fluid therethrough when the fluid level in the chamber has dropped to a predetermined level. The outlet port additionally includes an alignment member to properly align the floating disk member into proper engagement with the valve seat.

In accordance with one aspect of the invention, the fluid chamber includes a valve stem in which is formed an outlet port and having an alignment member projecting outwardly from the valve stem. The valve stem is formed with the valve seat at the top end thereof, through which the outlet port is formed. The floating disk member comprises a sealing member with an enlarged outer periphery. The sealing member is of a diameter large enough to fully cover the outlet port and valve seat. The floating disk member is constructed of a material having a specific gravity less than the fluid to be introduced into the chamber so that it will float in such fluid.

As fluid is introduced into the chamber, the floating disk member ascends with the fluid level remaining off the valve seat thus allowing flow of fluid out of the chamber. As fluid is depleted from the fluid chamber, the floating disk member descends along with the fluid level towards the bottom of the fluid chamber until it contacts and seals against the valve seat or contacts the alignment member which cooperates with the enlarged periphery of the floating disk member to align the sealing member over and into engagement with the valve seat closing the outlet port to prohibit the passage of fluid therethrough.

In a further aspect, the floating disk member comprises a disk-shaped membrane with an enlarged outer periphery in the shape of a toroid mounted to or forming a part of the membrane. In one aspect, the toroid and membrane are assembled together to form the floating member and in another aspect, they are formed as a single piece.

In another aspect of the invention, the fluid chamber is formed generally as a cylinder except for a downwardly converging tapered portion. The alignment member is disposed generally within the tapered portion so that as fluid is depleted from the chamber, and as the floating disk member consequently descends, the toroid of the floating disk member will contact the tapered portion of the chamber and the alignment member to align the disk properly with the valve seat.

In accordance with further more detailed aspects of the invention, the top of the valve stem is formed with a projecting frustoconical converging alignment surface and the toroid of the floating disk member is formed with an inwardly converging frustoconical guide surface. As fluid is depleted from the chamber and the floating disk member consequently descends, the converging alignment surface on the top of the valve stem and the guide surface in the toroid cooperate with each other to properly align the sealing membrane over and into sealing engagement with the valve seat.

The side wall of the chamber comprises a flexible resilient material and the alignment member is mounted on the valve stem so that there is space between it and the side wall of the chamber. This space permits an attendant to deform the side wall inwardly to dislodge the floating disk member from the valve seat when necessary.

In a more particular aspect of the invention, the alignment member includes a plurality of fins that extend radially outwardly from the valve stem. The fins are positioned to engage the toroid of the floating disk to urge the disk over the valve seat to properly seat the disk on the outlet port. Yet in a further aspect of the invention, the alignment member includes additional fins mounted on the inside surface of the chamber projecting inwardly toward the valve stem and leaving space between their ends and the valve stem for deformation of the chamber to dislodge a seated disk. In the event that the chamber is tilted, one or more of these shoulders will engage the toroid to align the disk properly with the valve seat.

In another detailed aspect of the invention, the valve stem, alignment member, and fluid chamber may be formed as a single unitary component, or the valve stem and alignment member may be slid into position as a retrofit of existing fluid chambers. The floating disk may be formed of multiple components bonded together or as a single component also.

Other features and advantages of the invention will become apparent from the following detailed description taken in conjunction with the accompanying drawings, which illustrate by way of example, the features and advantages of the invention.

DETAILED DESCRIPTION OF THE PREFERRED EMBODIMENTS

Figure 1:
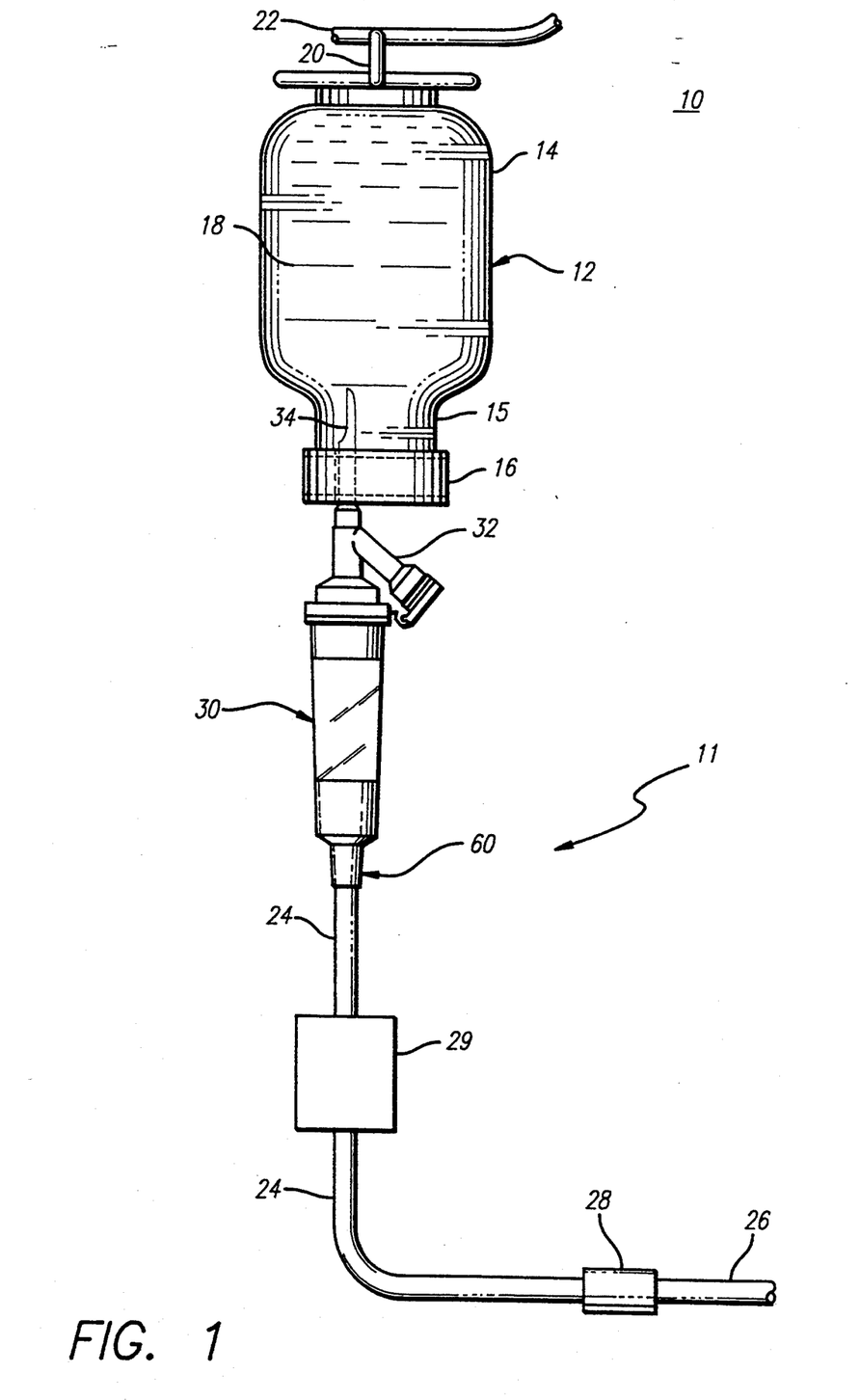
FIG. 1 is an overall view of a therapeutic fluid administration system showing an inverted parenteral fluid container connected to a parenteral fluid administration set, the set including a drip chamber containing the fluid shut off valve of the invention therein.

In the following description, like reference numerals will be used to refer to like or corresponding elements among the different figures of the drawings. Referring now to the drawings and particularly to FIG. 1, there is shown a parenteral fluid intravenous infusion system 10 having an administration set 11 in fluid communication with an inverted parenteral fluid container 12. The administration set includes a fluid shut off valve in accordance with principles of the present invention.

As shown in FIG. 1, the inverted parenteral fluid container 12 has a bottle shaped reservoir 14 including a hook mechanism 20 on the bottom end thereof connected to support rod 22 of a stand (not shown). The bottle reservoir has a reduced diameter neck 15 having a stopper 16 disposed therein.

The parenteral fluid administration set 11, typical of some of those used in the art, includes a drip chamber 30. For purposes of illustration, the shut off valve of the invention is shown for use with the drip chamber 30. However, a fluid shut off valve constructed in accordance with the invention may be incorporated in other types of fluid administration sets and other types of fluid monitoring and regulating devices not shown here, such as burettes.

The drip chamber 30 of the administration set 11 has an inlet and an outlet port, the outlet port 60 formed at the bottom end thereof and connected to a length of tubing 24. The distal end of the tubing is connected to a cannula 26 and attached to the tubing at a needle hub 28. In operation the cannula would be introduced into a patient's blood vessel for administration of the parenteral fluid. The drip chamber in this case is transparent, thereby providing a means to visually monitor fluid flow passing through the administration set and into a patient's blood stream. A fluid flow control device 29, such as a volumetric pump, is provided to regulate the flow rate of parenteral fluid through the administration set.

Figure 2:
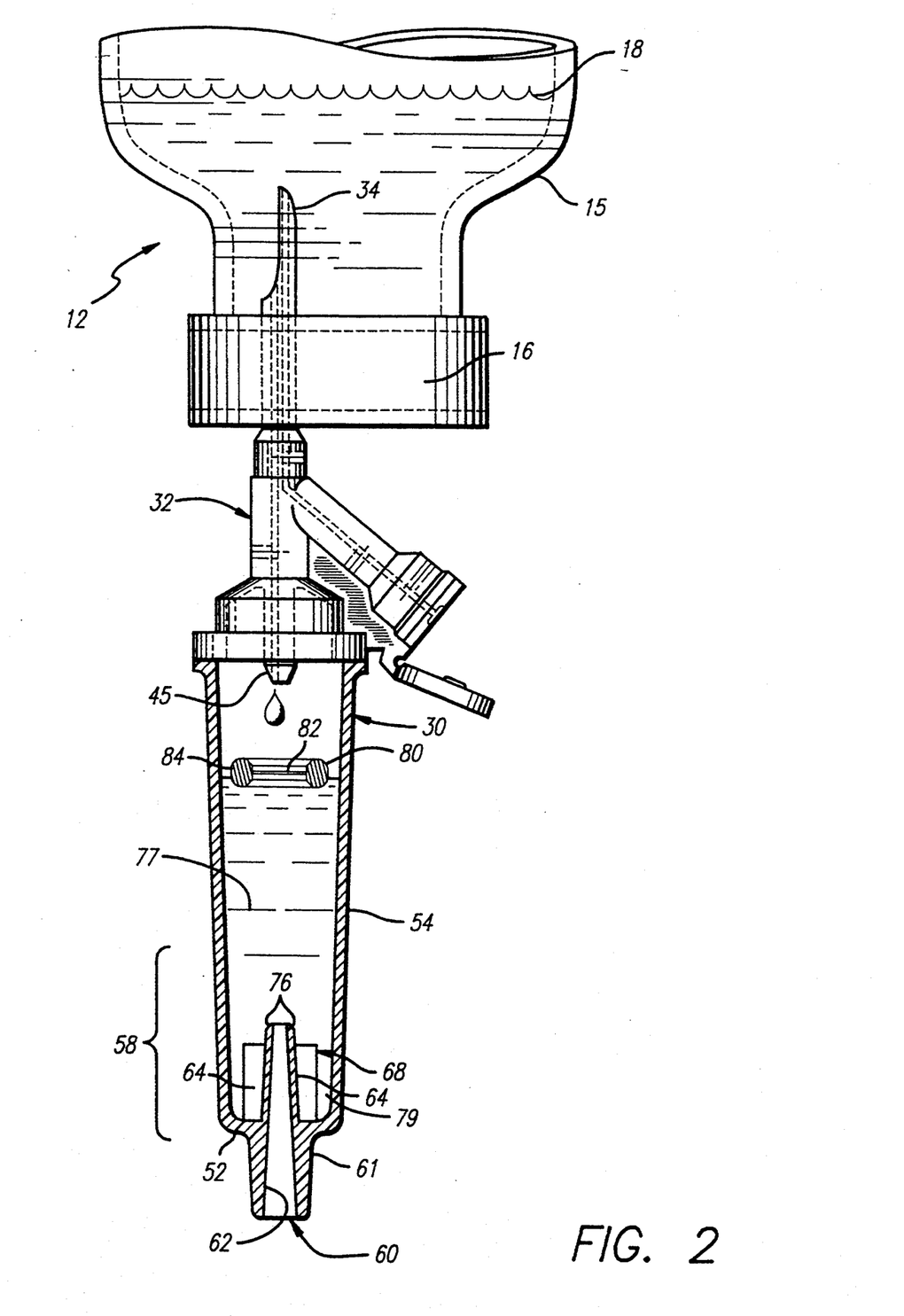
FIG. 2 is an enlarged partial sectional side view of the drip chamber shown in FIG. 1 showing the shut off valve depicted in an open state wherein the float member is not seated on the valve seat and in addition illustrating the alignment member and valve stem of the invention constructed integrally with the chamber.

The drip chamber 30 is connected to a vented penetrant assembly 32 having an upwardly extending spike 34, the top end thereof converging to a sharpened point. As shown in FIGS. 1 and 2, the spike has been inserted through the stopper 16 of the parenteral fluid container 12, and the top end of the spike is placed in fluid communication with the parenteral fluid 18 contained in the reservoir 14. The spike is vented so that air replaces the volume of fluid flowing out of the fluid reservoir during fluid administration.

Figure 3:
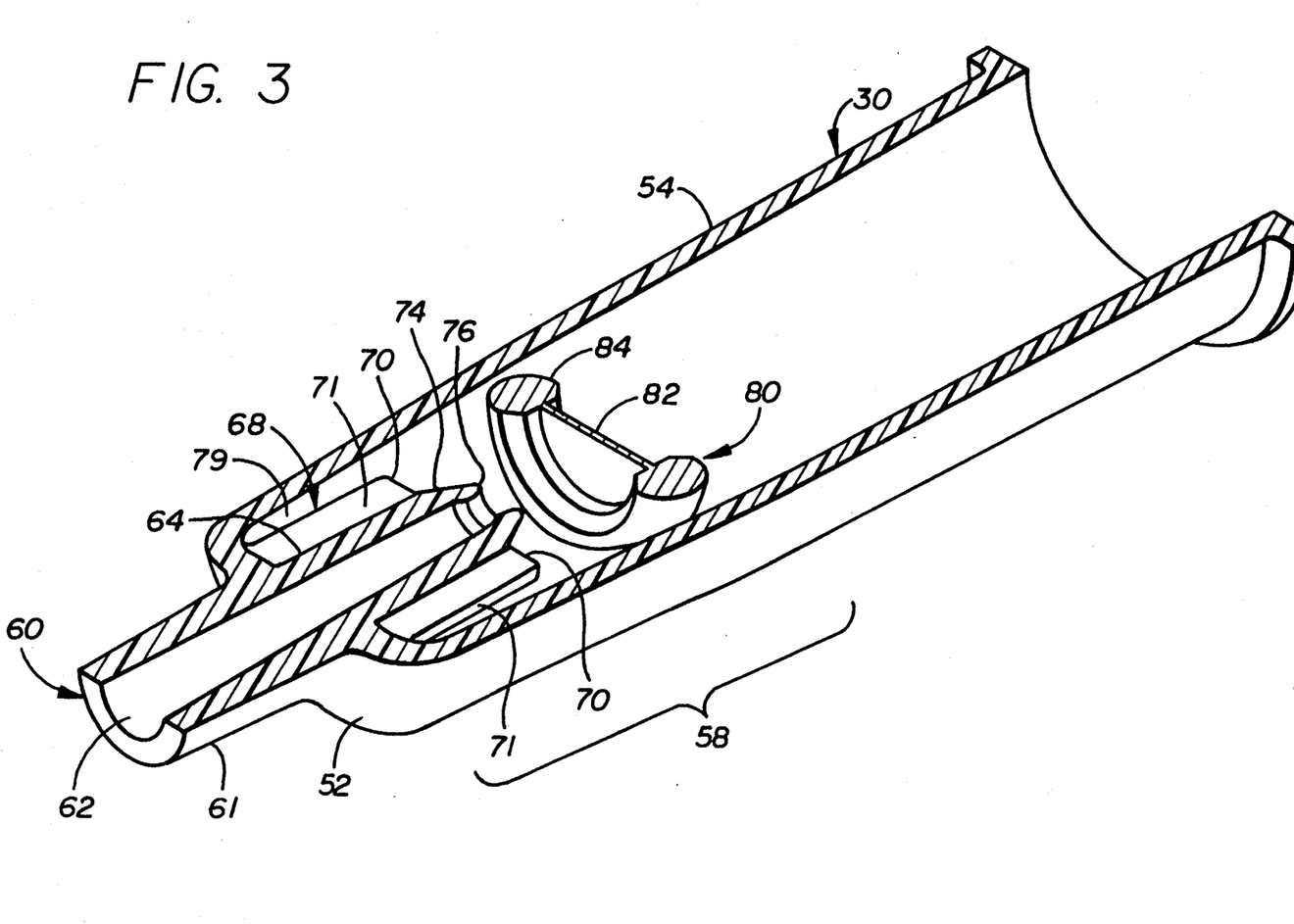
FIG. 3 is an enlarged sectional perspective view of the drip chamber shown in FIG. 2.

Referring more particularly to FIGS. 2 and 3, a fluid shut off valve constructed in accordance with the invention will be described in detail. The drip chamber 30 has a bottom wall 52 with a generally cylindrical side wall 54 although in this case, the cylindrical side wall tapers somewhat toward the bottom wall 52. The side wall comprises a flexible, resilient material, such as polyvinyl chloride (PVC) providing the ability for a hospital attendant to manually deform the side wall inwardly; the benefits of such a feature described below. Projecting downwardly from the bottom wall of the chamber is a generally cylindrical outlet stem 61 for connection to fluid tubing. A valve seat stem 64 projects inwardly from the bottom wall 52 into the fluid chamber. The valve stem 64 is generally cylindrical and is disposed concentrically within the tapered portion 58 of the cylindrical chamber side wall 54. The valve stem 64 in this embodiment is formed with a radially outward extending cylindrical alignment member 68, the top edge of the alignment member defining an alignment surface 70. In the preferred embodiment, the alignment member comprises a plurality of radially extending fins 71 (see FIG. 3) located equidistantly from each other about the valve stem. In this embodiment, the alignment member 68 does not touch the cylindrical side wall but leaves a space between it and the side wall for deformation of the wall to dislodge a seated disk, as is discussed below. The space between the alignment member 68 and the inner diameter of the side wall 54 forms an open volume 79, where parenteral fluid may accumulate. The top of the valve stem is formed with an inwardly converging frustoconical sloping alignment surface 74, the top end thereof projecting farther into the drip chamber. An axial bore 62 is formed through the valve stem 64 from the top of the frustoconical sloping surface 74 downwardly through the outlet stem 61 to define the drip chamber outlet port 60. At the top end of the frustoconical sloping surface, the intersection thereof with the axial bore defines an annular valve seat 76.

In the preferred embodiment as shown in FIG. 2, the drip chamber 30, including the valve stem 64 and the alignment member 68 are formed as one piece by an injection molding process or other process providing a singular unitary body. In all embodiments of the invention illustrated herein, the drip chamber is constructed of a somewhat flexible and resilient material. This material may be transparent so that one may visually monitor the flow rate and level of the parenteral fluid in the drip chamber.

Figure 4:
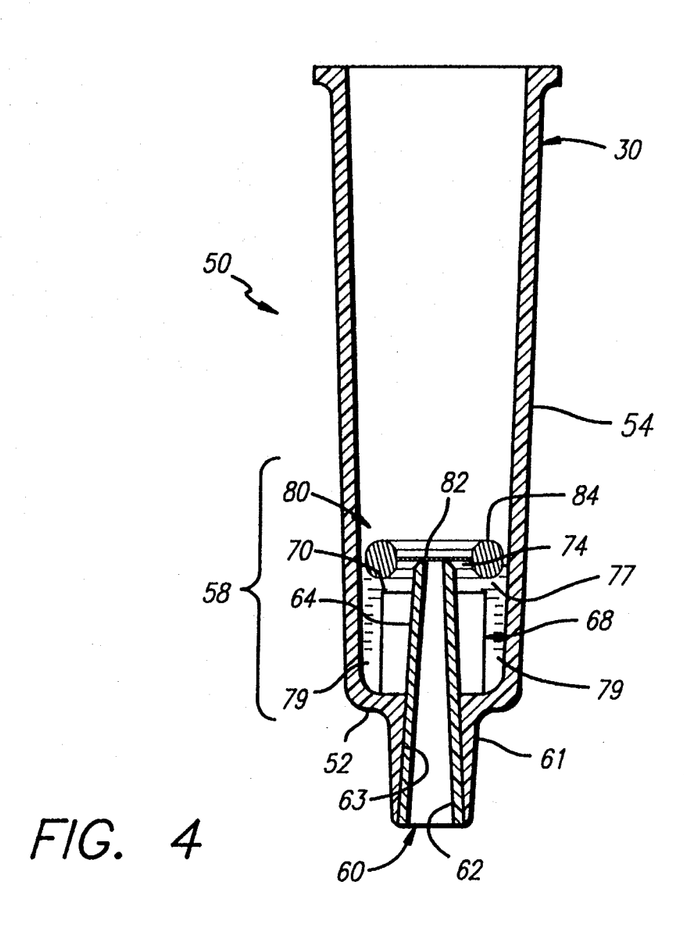
FIG. 4 is a sectional side view of the drip chamber similar to that shown in FIG. 2, showing the shut off valve in a closed state and depicting an alternative embodiment of the invention wherein the alignment member and fluid chamber are constructed in two pieces.
Figure 5:
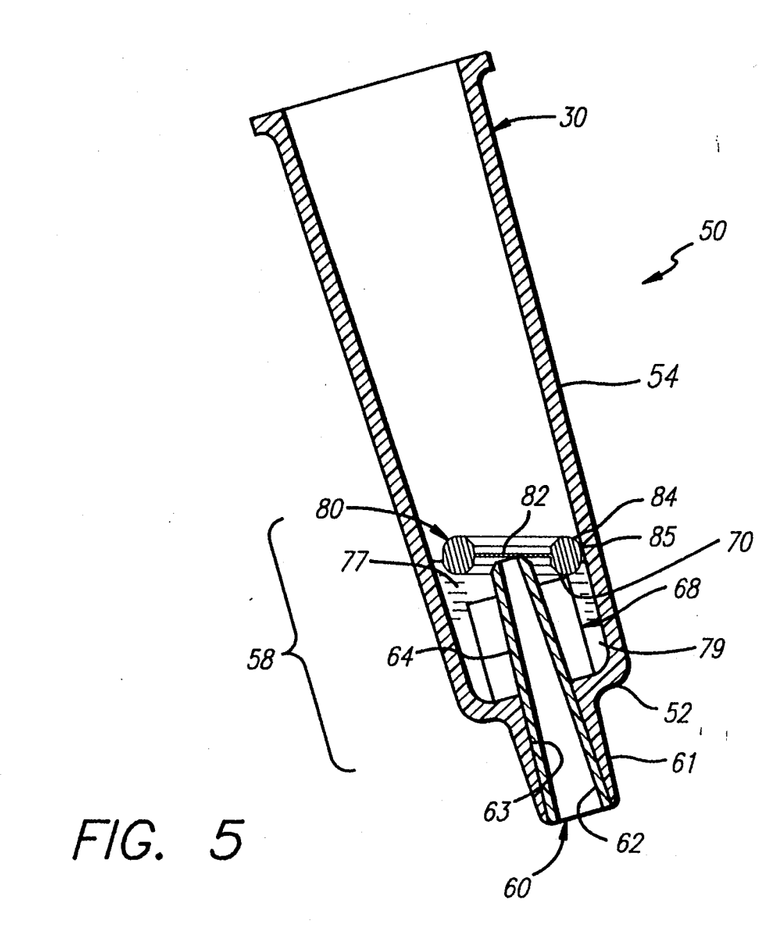
FIG. 5 is a side view of the drip chamber similar to that shown in FIG. 4 tilted to one side, and illustrating cooperation between the float member and alignment member to close the shut off valve.

In the alternative embodiment shown in FIGS. 4 and 5, a two piece fluid chamber 50 construction is provided. The first piece is the drip chamber itself 30 with its side wall 54, bottom wall 52, and an outlet stem 61 with an alignment bore 63 in the outlet stem. The second piece includes the valve stem 64 and the alignment member 68. The valve stem 64 in this case is long enough to fit tightly into the alignment bore 63 of the outlet stem 61 to become a part of the outlet port. The valve stem 64 is received within the alignment bore 63 and the two components are bonded together utilizing a suitable adhesive to provide secure engagement therebetween while providing a liquid tight seal. In some cases, the valve stem and alignment member may be configured for assembly in a conventional drip chamber.

Figure 6:
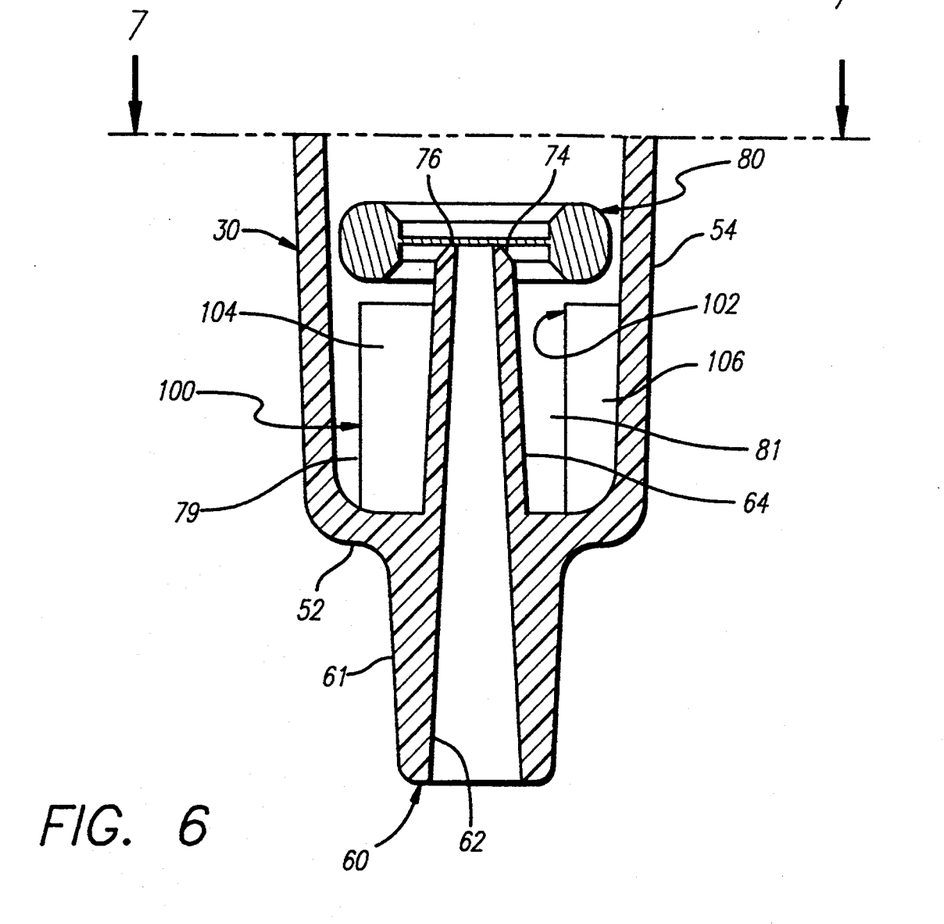
FIG. 6 is an enlarged sectional partial side view of a drip chamber depicting an alternative embodiment of the invention wherein alignment members extend both radially outwardly from the valve stem and project radially inwardly from the chamber side wall.
Figure 7:
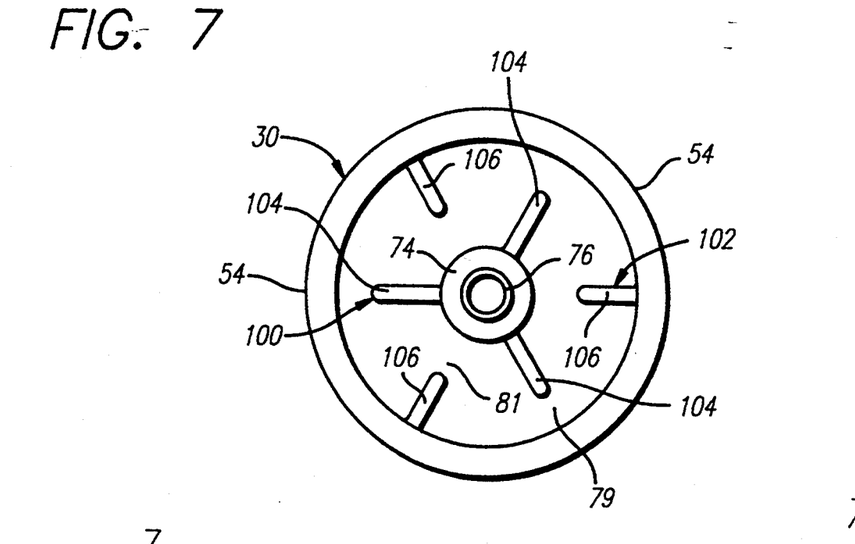
FIG. 7 is an enlarged view taken along lines 7—7 of FIG. 6 without the floating disk shown in FIG. 6.

In an alternate embodiment as shown in FIGS. 6 and 7, the drip chamber 30 is formed as a single unitary body; however, the alignment member is formed in two pieces having inner and outer alignment members, 100 and 102 respectively. The inner alignment member 100 is formed so that it extends radially outwardly from the valve stem 64 and in this embodiment, includes a plurality of equally spaced-apart inner fins 104. The outer alignment member 102 is formed so that it extends radially inwardly from the cylindrical side wall 54 and in this embodiment, has a plurality of inwardly projecting equally spaced-apart outer fins 106. The inner alignment member does not extend radially outwardly far enough to meet the side wall 54 and the outer alignment member does not extend radially inwardly far enough to meet the valve stem 64. Because of this arrangement, the side wall may still be deformed inwardly for a distance to dislodge a seated disk. A second open volume 81 is maintained between the outer alignment member 102 and the valve stem 64.

Returning now to FIG. 2, a predetermined amount of parenteral fluid 77 has accumulated in the drip chamber 30. A float valve member, generally indicated by numeral 80, is provided and is formed of a material or materials having a lower specific gravity than the parenteral fluid. The float member 80 is therefore buoyant and floats in the fluid. The float valve member 80 comprises a sealing member 82 and an enlarged portion 84 joined around the periphery of the sealing member 82. In the preferred embodiment, the sealing member is in the form of a thin disk membrane and the enlarged portion is generally in the form of a toroidal member. Taken together, they are referred to as a floating disk member.

Figure 8:
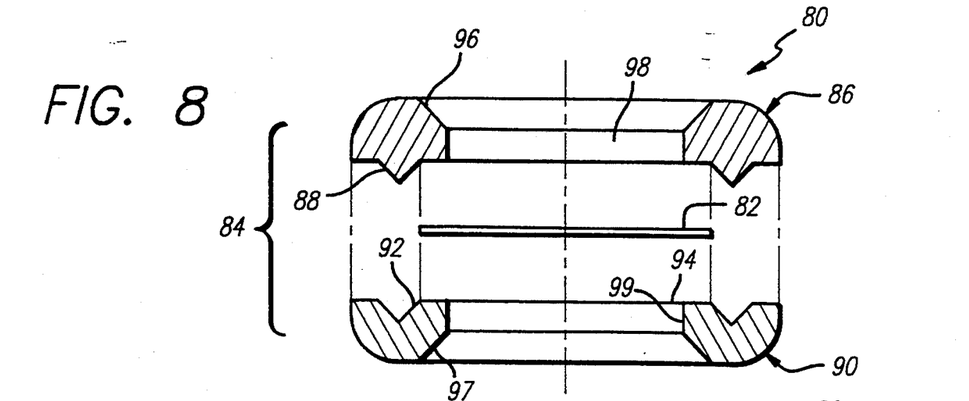
FIG. 8 is an enlarged exploded sectional side view of a multi-component float member of the invention.
Figure 9:
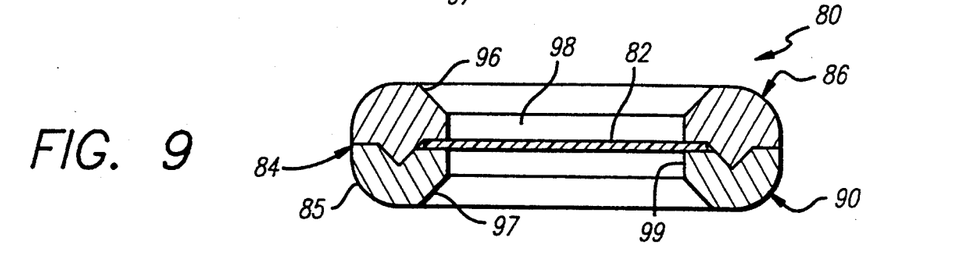
FIG. 9 is an assembled sectional side view of the multi-component float member shown in FIG. 8.

In one embodiment of the invention, the floating disk member 80 is of multiple component construction. With reference now to FIGS. 8 and 9, one embodiment of such a construction can be seen. The toroidal member 84 includes a top half 86 and a bottom half 90 that sandwich the disk membrane 82 between themselves. In general, the top half of the float member is formed as the top half of a toroid split along a transverse plane at the major diameter thereof. The top half is formed with a downwardly projecting annular triangular ridge 88. The inner diameter of the toroidal member 84 is formed with a smooth cylindrical inner surface 98. A smooth inwardly converging frustoconical guide surface 96 is formed from the top of the toroid converging inwardly and downwardly to meet the cylindrical surface 98.

The bottom half 90 of the toroidal member 84 is essentially the mirror image of the top half 86 except that it includes an annular triangular depression 92. The annular depression 92 is complementarily shaped to the annular ridge 88 for receipt of the annular ridge therein. As with the top half, the bottom half 90 of the toroidal member is formed at its inner diameter with a generally smooth cylindrical surface 99 of substantially the same diameter as the cylindrical surface 98 of the top half. Likewise, the bottom half of the toroidal member is formed with a frustoconical inwardly converging guide surface 97. In addition, the bottom half of the toroidal member includes an annular recess 94 between the inner top edge of the annular depression 92 and the bottom cylindrical surface 99 to receive the disk membrane 82.

The thin disk membrane 82 is held between the top and bottom halves 86 and 90 by pressure and adhesive. The thin disk membrane 82 is formed of a flexible resilient material such as synthetic rubber, such as NATSYN ™ available from Goodyear, having an outer diameter generally the same diameter as the outer diameter of the annular recess 94. The disk membrane is of a thickness substantially the same width as the recessed extent of the annular seat 94. In one embodiment, the disk thickness was 0.127 mm (0.005 inches).

In the assembled configuration, as shown in FIG. 9, the top 86 and bottom 90 halves of the toroid sandwich the outer periphery of the flexible disk membrane 82 between the annular recessed seat 94 and the bottom surface of the top half. The periphery of the disk membrane and the annular projection 88 and depression 92 are securely bonded together using a suitable adhesive which is impervious to parenteral fluids. In such an assembled configuration, the toroidal member 84 has a smooth generally rounded outer surface 85.

Figure 10:
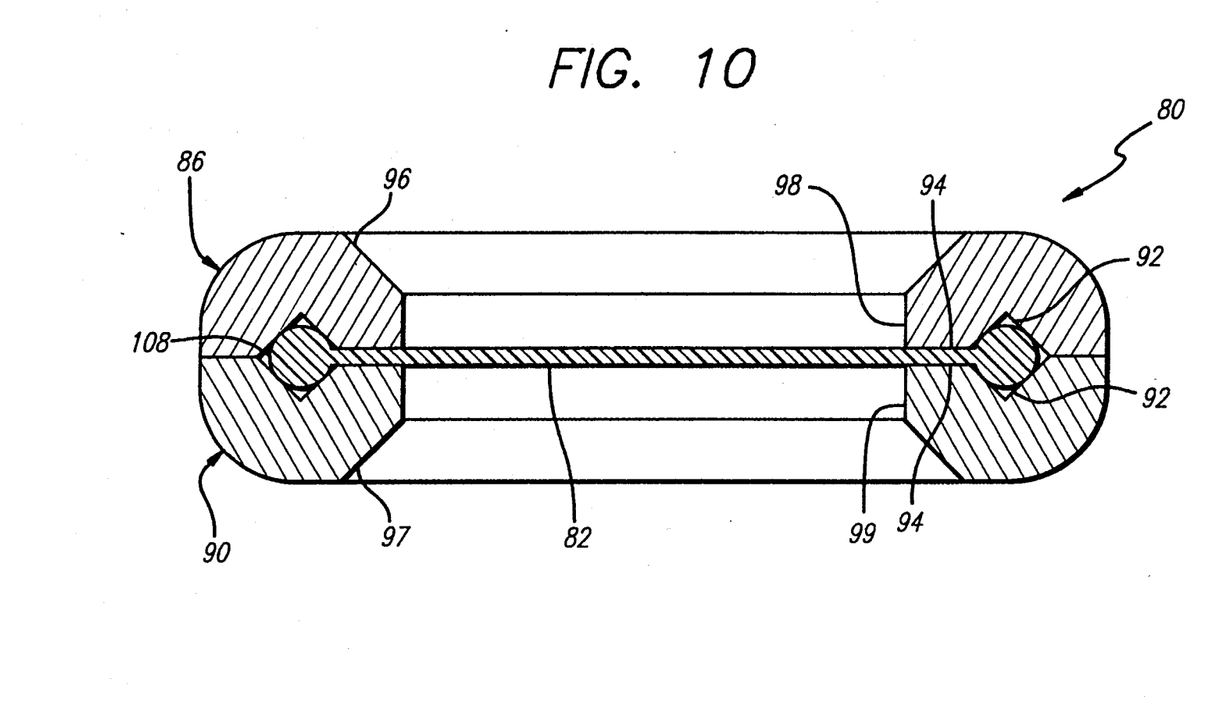
FIG. 10 is an assembled sectional side view of an alternative embodiment of a multi-component float member.

In another multi-component embodiment of the floating disk member 80 as shown in FIG. 10, the floating disk member 80 has identical top and bottom halves, 86 and 90 respectively. Each is formed with an annular triangular depression 92 and annular recess 94 similar to that described above with respect to the bottom half 90 in FIGS. 8 and 9. The floating disk member of FIG. 10 is likewise formed with smooth cylindrical inner surfaces 98 and 99 and inwardly converging guide surfaces 96 and 97. However, in this embodiment the thin membrane 82 has an enlarged outer periphery 108 for mounting within the annular depressions 92 of the top and bottom toroid halves 86 and 90.

Figure 11:
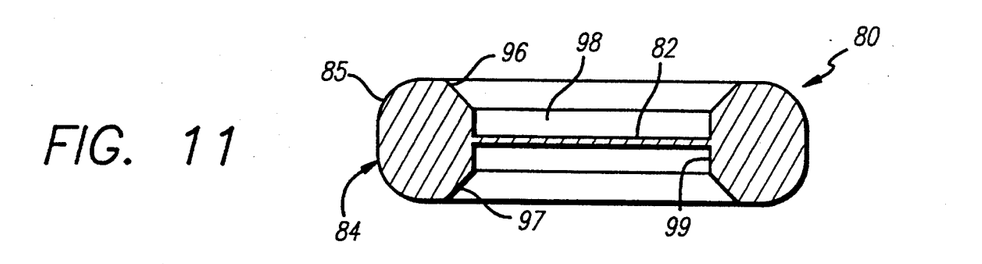
FIG. 11 is a sectional side view of a floating disk member wherein the sealing membrane and toroid member are formed as a single piece.

In the alternate embodiment shown in FIG. 11, the floating disk member 80 is constructed as a single unitary body. The floating disk member 80 of FIG. 11 is essentially constructed to have the same external shape and size as the multi-component embodiments illustrated in FIGS. 8, 9, and 10 and therefore will not be described in detail. The one piece float member may be manufactured utilizing an injection molding process or other processes and may be formed also of synthetic rubber. It has been found that a floating disk member of unitary construction as shown in FIG. 11 can be made less expensively than some multi-component constructions, yet functions as well or better. In the case of some prior floating disks, the membrane would be formed of silicone that has a higher specific gravity than many parenteral fluids. The toroid would then have to be made of a material having a lower specific gravity, such as polyethylene. In some cases, this combination resulted in a device having a higher specific gravity than one made in accordance with FIG. 11 using synthetic rubber.

Figure 12:
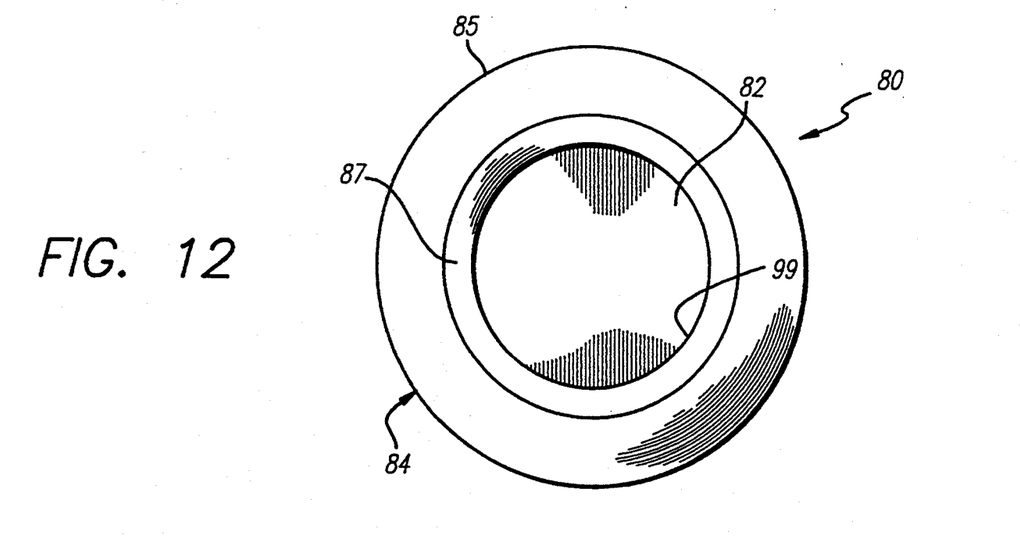
FIG. 12 is a bottom view of the floating disk member depicted in FIGS. 8, 9, 10, and 11.

A bottom view of FIG. 11 is shown in FIG. 12. The toroidal member 84 completely encloses the disk membrane 82. The diameter of the disk membrane is sufficient to fully cover the valve seat 76 of the valve stem 64. The inwardly converging frustoconical guide surface 97 and the smooth rounded outer surface 85 are also shown.

Returning to FIGS. 1, 2 and 4, the operation and use of the fluid shut off valve will now be discussed. During administration of parenteral fluid, the fluid 18 flows from the fluid container 12 through a fluid duct in the vented penetrant assembly 32 out of an inlet port 45 and drips into the drip chamber 30. As the fluid accumulates in the chamber, the level thereof ascends in the fluid chamber carrying the floating disk 80 at the surface thereof. Because of its symmetrical shape, the floating disk may float on either of its sides. This arrangement eliminates the need to design an apparatus for keeping the float member in a specific "upright" orientation. In addition, the generally flat shape of the disk 80 inhibits its tendency to bob in the fluid and prematurely seat during high flow rates.

As the parenteral fluid 77 in the drip chamber 30 is depleted, the surface level thereof descends, carrying the floating disk 80 with it. During the disk's descent towards the valve seat, the circular outer surface of the toroidal member 84 may contact and ride downwardly along the inner surface of the cylindrical side wall 54 of the drip chamber. As the parenteral fluid continues to descend, the rounded outer surface of the float member may contact the tapered side wall 58 of the drip chamber, the tapered portion urging the disk membrane 82 of the float member into alignment over the annular valve seat 76 of the valve stem 64. As stated above, the diameter of the disk membrane 82 is large enough to fully cover the annular valve seat.

The outer diameter of the toroidal member 84 is less in diameter than the inner diameter of the cylindrical tapered side wall 58 at the alignment surface 70 of the alignment member 68. With such configuration, the float member 80 can descend to the valve seat 76 without interference by the side wall 58. As the disk nears the valve seat, the frustoconical guide surface 74 of the valve stem 64 will cooperate with the frustoconical guide surface 97 of the toroidal member to assist in aligning the disk membrane 82 over the annular valve seat 76 until the membrane finally seals the outlet port stopping the flow of fluid.

In the case where the drip chamber is tilted as shown in FIG. 5, the toroidal member 84 of the floating disk will contact the alignment surface 70 of the alignment member 68. The alignment surface will hold that part of the floating disk in position until the fluid level further descends sufficiently to allow the membrane of the disk to seal against the valve seat. As can be seen from FIGS. 4, 5, and 6, the annular valve seat 76 is disposed above the alignment shoulder by a distance greater than the distance between the surface of the disk membrane and the outer surface of the toroidal member. This configuration results in the efficient seating of the membrane on the valve seat even when the drip chamber 30 is tilted to one side.

As shown in FIGS. 4 and 6, the fluid level in the drip chamber 30 has been sufficiently depleted so that the fluid shut off valve is in its closed condition. In such state, the disk membrane 82 of the disk 80 is in sealing engagement with the valve seat 76 to close the outlet port 60 to stop the passage of air therethrough. The seal between the disk membrane and the valve seat may be enhanced as the parenteral fluid contained in the tubing 24 below the outlet port creates a suction pressure head due to the force of gravity acting on such fluid or as a volumetric pump "dead heads" as it pumps against the valve seat.

In the case where an empty fluid reservoir 12 is to be replaced with a full reservoir and flow resumed through the drip chamber, a seated disk must be dislodged from the valve seat to allow flow to resume. After installing the new fluid reservoir 12, the attendant will deform the side wall of the drip chamber inward to dislodge the disk from the valve seat 76. Flow can then resume. In some cases, a suction pressure head may have been created between the valve seat and the disk membrane 82 thus requiring increased force to dislodge the disk. However, the arrangement in accordance with the invention makes dislodging the disk easier. Because the side wall of the drip chamber is relatively straight and the outer surface 85 of the disk is rounded, less force will be required to deform the side wall inward and release the disk. This is true in both embodiments of the alignment surfaces shown in FIGS. 3 and 6. The attendant grasps opposing tapered portions 58 of the side wall 54 between his or her thumb and forefinger to slightly compress the resilient side wall inward. The inner surface of the deformed wall contacts the rounded outer surface 85 of the toroidal member 84 to force the disk upward and off the valve seat. The rounded outer surface 85 of the disk assists in this dislodging procedure. Because the outer fins 106 mounted on the inside surface of the side wall 54 are oriented vertically, they do not substantially increase the amount of force required to inwardly deform the side wall 54.

The materials of construction utilized in the manufacture of the drip chamber 30, valve stem 64, and float member 80 are such that they are compatible with the parenteral fluid selected for administration to a patient.

The arrangement of the side wall 54, drip chamber 30, valve stem 64, and alignment member are such that they cooperate effectively to align the sealing member 82 of the floating disk member 80 over the valve seat 76 as fluid is depleted from the drip chamber. The sealing member will engage the valve seat and provide an effective seal even if the drip chamber is tilted to one side. The arrangement also facilitates the release of the disk that has sealed against the valve seat.

It will be apparent from the foregoing that, while particular forms of the invention have been illustrated and described, various modifications can be made without departing from the spirit and scope of the invention.

Accordingly, it is not intended that the invention be limited, except as by the appended claims.

What is claimed is:

1. A fluid flow shut-off valve for controlling the flow of fluid through a fluid conduit, the fluid conduit connected between a parenteral fluid reservoir and a patient, the valve comprising:

a fluid chamber connected in line with the fluid conduit to accumulate parenteral fluid, the chamber comprising:
 a first end having an inlet port;
 a second end having an opening;
 a side wall connecting and disposed between the first end and to the second end;
 a valve seat stem mounted at the opening in the second end and having a valve seat projecting into the chamber, the valve seat having a bore therethrough defining an outlet port connected to the opening in the second end, the stem having a size such that there is a first distance between it and the side wall;
 an alignment member disposed between the valve stem and the side wall and having a size selected to be smaller than the first distance so that the side wall can be deformed inwardly towards the valve stem, the alignment member having an alignment surface thereon; and
a floating disk member located in the chamber, the floating disk member formed such that it floats in the fluid accumulated in the chamber, the floating disk member comprising:
 a sealing member having a size large enough to completely cover the valve seat and the outlet port; and
 an enlarged peripheral portion located at the periphery of the sealing member;
wherein the sidewall is deformable inwardly to dislodge the disk member from the valve seat, the outer surface of the portion of the side wall surrounding the valve stem is straight in the longitudinal axis and the alignment surface is positioned to engage the enlarged peripheral portion of the floating disk member to align the sealing member with the valve seat as fluid contained in the chamber is depleted.

2. The fluid valve of claim 1 wherein the alignment member comprises multiple alignment surfaces located at different positions about the valve seat.

3. The fluid valve of claim 2 wherein an alignment surface is mounted on the valve stem and an alignment surface is mounted on the inside of the side wall.

4. The fluid valve of claim 2 wherein the alignment member comprises a plurality of fins mounted to the valve stem and extending radially outwardly therefrom, each fin having a length that is less than the first distance.

5. The fluid valve of claim 2 wherein the alignment member comprises a plurality of fins mounted to the side wall of the chamber and extending inwardly therefrom, each fin having a length that is less than the first distance.

6. The fluid valve of claim 2 wherein the alignment member comprises a plurality of fins, some of which are mounted to the valve stem and extend outwardly therefrom and some of which are mounted to the side wall of the chamber and extend inwardly therefrom, each fin having a length that is less than the first distance.

7. The fluid valve of claim 1 wherein the sealing member is shaped in the form of a disk and the enlarged peripheral portion comprises a toroidal member surrounding the sealing member and having a rounded outer surface.

8. The fluid valve of claim 1 wherein the floating disk member comprises a sealing member surrounded by a toroidal member having a rounded outer surface, the sealing member and toroidal member being integrally formed as a one piece body.

9. The fluid valve of claim 1 wherein the valve seat further comprises a guide surface adapted to receive the floating disk member and guide it into a position where the sealing member engages the valve seat.

10. The fluid valve of claim 9 wherein the guide surface of the valve seat comprises a frustoconically-shaped surface for engaging the inside surface of the enlarged peripheral portion of the floating disk member.

11. The fluid valve of claim 1 wherein the floating disk member further comprises a guide surface adapted to receive the valve stem to guide itself into a position where the sealing member engages the valve seat.

12. The fluid valve of claim 11 wherein the guide surface of the floating disk member comprises an inwardly converging frustoconically-shaped surface formed on the enlarged peripheral portion.

13. The fluid valve of claim 1 wherein:
the valve seat further comprises a guide surface adapted to receive the floating disk member and guide it into a position where the sealing member engages the valve seat; and
the floating disk member further comprises a guide surface adapted to receive the valve stem to guide itself into a position where the sealing member engages the valve seat.

14. The fluid valve of claim 13 wherein:
the guide surface of the valve seat comprises a frustoconically-shaped surface for engaging the inside surface of the enlarged peripheral portion of the floating disk member; and
the guide surface of the floating disk member comprises an inwardly converging frustoconically-shaped surface formed on the enlarged peripheral portion.

15. The fluid valve of claim 1 wherein the fluid chamber and the alignment member are integrally formed as a one piece body.

16. The fluid valve of claim 1 wherein the valve stem and alignment member are integrally formed as a one piece body and are formed separately from the fluid chamber and are shaped for insertion into and bonding to the fluid chamber.

17. A fluid flow shut-off valve for controlling the flow of fluid through a fluid conduit, the fluid conduit connected between a parenteral fluid reservoir and a patient, the valve comprising:
a fluid chamber connected in line with the fluid conduit to accumulate parenteral fluid, the chamber comprising:
a first end having an inlet port;
a second end having an opening;
a side wall connecting and disposed between the first end and to the second end;
a valve seat stem mounted at the opening in the second end and having a valve seat projecting into the chamber, the valve seat having a bore therethrough defining an outlet port connected to the opening in the second end, the stem having a size such that there is a first distance between it and the side wall;
multiple alignment surfaces disposed between the valve stem and the side wall, each having a size selected to be smaller than the first distance so that the side wall can be deformed inwardly towards the valve stem; and a floating disk member located in the chamber, the floating disk member formed such that it floats in the fluid accumulated in the chamber, the floating disk member comprising:
a disk-shaped sealing member having a size large enough to completely cover the valve seat and the outlet port; and
a toroid member surrounding the sealing member and having a rounded outer surface;
wherein the sidewall is deformable inwardly to dislodge the disk member from the valve seat, the outer surface of the portion of the side wall surrounding the valve stem is straight in the longitudinal axis and the alignment surfaces are positioned to engage the enlarged peripheral portion of the floating disk member to align the sealing member with the valve seat as fluid contained in the chamber is depleted.

18. The fluid valve of claim 17 wherein the alignment surfaces comprise a plurality of fins mounted to the valve stem and extending radially outwardly therefrom, each fin having a length that is less than the first distance.

19. The fluid valve of claim 18 wherein the sealing member and toroidal member of the floating disk member are integrally formed as a one piece body.

20. A fluid flow shut-off valve for controlling the flow of fluid through a fluid conduit, the fluid conduit connected between a parenteral fluid reservoir and a patient, the valve comprising:
a fluid chamber connected in line with the fluid conduit to accumulate parenteral fluid, the chamber comprising:
a first end having an inlet port;
a second end having an opening;
a side wall connecting and disposed between the first end and the second end, the side wall being tapered toward the second end;
a valve seat stem mounted at the opening in the second end and having a valve seat projecting into the chamber, the valve seat having a bore therethrough defining an outlet port connected to the opening in the second end, the stem having a size such that there is a first distance between it and the side wall;
a plurality of fins, some of which are mounted to the valve stem and extend outwardly therefrom and some of which are mounted to the side wall of the chamber and extend inwardly therefrom, each fin having a length that is less than the first distance so that the side wall can be deformed inwardly towards the valve stem; and
a floating disk member located in the chamber, the floating disk member formed such that it floats in the fluid accumulated in the chamber, the floating disk member comprising:
a disk-shaped sealing membrane having a size large enough to completely cover the valve seat and the outlet port; and
a toroid member surrounding the sealing member and having a rounded outer surface;
wherein the sidewall is deformable inwardly to dislodge the disk member from the valve seat, the alignment surfaces are positioned to engage the enlarged peripheral portion of the floating disk member to align the sealing member with the valve seat as fluid contained in the chamber is depleted.

* * * * *